United States Patent
Hök et al.

(10) Patent No.: US 11,964,558 B2
(45) Date of Patent: Apr. 23, 2024

(54) SENSOR SYSTEM FOR PASSIVE IN-VEHICLE BREATH ALCOHOL ESTIMATION

(71) Applicant: Automotive Coalition for Traffic Safety, Inc., Sterling, VA (US)

(72) Inventors: Bertil Hök, Västerås (SE); Raimo Gester, Västerås (SE); Jonas Ljungblad, Stockholm (SE); Håkan Pettersson, Floda (SE)

(73) Assignee: Automotive Coalition for Traffic Safety, Inc., Leesburg, VA (US)

( * ) Notice: Subject to any disclaimer, the term of this patent is extended or adjusted under 35 U.S.C. 154(b) by 0 days.

(21) Appl. No.: 17/462,318

(22) Filed: Aug. 31, 2021

(65) Prior Publication Data
US 2022/0055478 A1 Feb. 24, 2022

Related U.S. Application Data

(63) Continuation of application No. 15/389,724, filed on Dec. 23, 2016, now Pat. No. 11,104,227.

(60) Provisional application No. 62/312,476, filed on Mar. 24, 2016.

(51) Int. Cl.
*G06F 17/00* (2019.01)
*B60K 28/06* (2006.01)
*G01N 33/00* (2006.01)
*G01N 33/497* (2006.01)

(52) U.S. Cl.
CPC ....... *B60K 28/063* (2013.01); *G01N 33/0067* (2013.01); *G01N 33/4972* (2013.01)

(58) Field of Classification Search
CPC .. B60K 28/06; B60K 28/063; G01N 33/0067; G01N 33/4972
USPC .............................................................. 701/1
See application file for complete search history.

(56) References Cited

U.S. PATENT DOCUMENTS

| | | | |
|---|---|---|---|
| 3,301,482 A | 1/1967 | Bullen |
| 3,780,311 A | 12/1973 | Brown |
| 3,792,272 A | 2/1974 | Harte et al. |
| 3,792,351 A | 2/1974 | Ireland |
| 3,830,630 A | 8/1974 | Kiefer et al. |
| 3,897,659 A | 8/1975 | Henry |

(Continued)

FOREIGN PATENT DOCUMENTS

| | | |
|---|---|---|
| CN | 1586944 | 3/2005 |
| CN | 101292158 | 10/2008 |

(Continued)

OTHER PUBLICATIONS

Development and Evaluation of Algorithms for Breath Alcohol Screening (Year: 2016).*

(Continued)

*Primary Examiner* — Ronnie M Mancho
(74) *Attorney, Agent, or Firm* — Pandiscio & Pandiscio

(57) ABSTRACT

Methods and apparatus allow for passive determination of a driver's Breath Alcohol Concentration (BrAC). Alcohol concentrations can be determined from exhaled breath, however inconvenience to a driver is often a barrier for incorporation of BrAC sensors into vehicles. The methods and apparatus allow for passive determination of a driver's BrAC, while detecting and accounting for a wide range of environmental conditions that may reduce the accuracy of a passive BrAC reading.

20 Claims, 5 Drawing Sheets

(56) References Cited

U.S. PATENT DOCUMENTS

| | | |
|---|---|---|
| 4,090,078 A | 5/1978 | Heim |
| 4,294,327 A | 10/1981 | Howard |
| 4,535,620 A | 8/1985 | Cunningham |
| 4,678,057 A | 7/1987 | Elfman et al. |
| 4,749,553 A | 6/1988 | Lopez et al. |
| 4,843,377 A | 6/1989 | Fuller et al. |
| 4,868,545 A | 9/1989 | Jones |
| 4,916,435 A | 4/1990 | Fuller |
| 4,975,581 A | 12/1990 | Robinson et al. |
| 4,996,161 A | 2/1991 | Conners et al. |
| 5,006,315 A | 4/1991 | Maroulis et al. |
| 5,303,575 A | 4/1994 | Brown et al. |
| 5,426,415 A | 6/1995 | Prachar et al. |
| 5,458,853 A | 10/1995 | Porter et al. |
| 5,485,850 A | 1/1996 | Dietz |
| 5,544,276 A | 8/1996 | Loux et al. |
| 3,283,563 A | 11/1996 | Turner et al. |
| 5,652,398 A | 7/1997 | Johnson |
| 5,655,530 A | 8/1997 | Messerschmidt |
| 5,693,944 A | 12/1997 | Rich |
| 5,746,973 A | 5/1998 | Naraqhi |
| 5,823,951 A | 10/1998 | Messerschmidt |
| 5,830,112 A | 11/1998 | Wanq et al. |
| 5,877,345 A | 3/1999 | Bauer et al. |
| 5,906,203 A | 5/1999 | Klockseth et al. |
| 5,955,886 A | 9/1999 | Cohen et al. |
| 5,971,937 A | 10/1999 | Ekstrom |
| 6,123,674 A | 9/2000 | Rich |
| 6,129,680 A | 10/2000 | Mottram |
| 6,142,951 A | 11/2000 | Park |
| 6,152,876 A | 11/2000 | Robinson et al. |
| 6,157,041 A | 12/2000 | Thomas et al. |
| 6,229,908 B1 | 5/2001 | Edmonds et al. |
| 6,266,353 B1 | 7/2001 | Freitas et al. |
| 6,441,388 B1 | 8/2002 | Thomas et al. |
| 6,468,222 B1 | 10/2002 | Mault et al. |
| 6,488,635 B1 | 12/2002 | Mottram |
| 6,528,809 B1 | 3/2003 | Thomas et al. |
| 6,608,399 B2 | 8/2003 | McConnell et al. |
| 6,622,032 B1 | 9/2003 | Robinson et al. |
| 6,684,099 B2 | 1/2004 | Ridder et al. |
| 6,726,636 B2 | 4/2004 | Der Ghazarian et al. |
| 6,748,301 B1 | 6/2004 | Ryu |
| 6,794,988 B1 | 9/2004 | Weiss et al. |
| 6,862,091 B2 | 3/2005 | Johnson |
| 6,983,176 B2 | 1/2006 | Gardner et al. |
| 7,016,713 B2 | 3/2006 | Gardner et al. |
| 7,092,832 B2 | 8/2006 | Brown |
| 7,098,037 B2 | 8/2006 | Haas et al. |
| 7,173,524 B2 | 2/2007 | Ponziani |
| 7,202,091 B2 | 4/2007 | Jones et al. |
| 7,386,152 B2 | 6/2008 | Rowe et al. |
| 7,446,878 B2 | 11/2008 | Ridder et al. |
| 7,671,752 B2 | 3/2010 | Sofer |
| 7,736,903 B2 | 6/2010 | Lambert et al. |
| 7,764,982 B2 | 7/2010 | Dalke et al. |
| 7,848,605 B2 | 12/2010 | Ridder et al. |
| 7,993,281 B2 | 8/2011 | Stock et al. |
| 8,306,595 B2 | 11/2012 | Osaki et al. |
| 8,469,134 B2 | 6/2013 | Osaki et al. |
| 8,605,959 B2 | 12/2013 | Kangas |
| 8,773,390 B1 | 7/2014 | Clark |
| 9,068,885 B2 | 6/2015 | Kluczynski et al. |
| 9,073,431 B2 | 7/2015 | Takahashi |
| 9,163,718 B2 | 10/2015 | Nelson |
| 9,823,237 B2 | 11/2017 | Martin et al. |
| 10,151,744 B2 | 12/2018 | Hok et al. |
| 11,104,227 B2 | 8/2021 | Hok et al. |
| 11,391,724 B2 * | 7/2022 | Hok ............ A61B 5/0059 |
| 2002/0084130 A1 | 7/2002 | Der Ghazarian et al. |
| 2002/0140289 A1 | 10/2002 | McConnell et al. |
| 2003/0039299 A1 | 2/2003 | Horovitz |
| 2003/0048000 A1 | 3/2003 | Harter |
| 2003/0085284 A1 | 5/2003 | Bremer et al. |
| 2004/0093957 A1 | 5/2004 | Buess et al. |
| 2004/0260194 A1 | 12/2004 | Baver |
| 2005/0241871 A1 | 11/2005 | Stewart et al. |
| 2006/0058697 A1 | 3/2006 | Mochizuki et al. |
| 2006/0153740 A1* | 7/2006 | Sultan ............ G01N 21/61 422/88 |
| 2006/0154377 A1* | 7/2006 | Lambert ............ G01N 21/05 436/167 |
| 2006/0167349 A1 | 7/2006 | Gardner et al. |
| 2006/0206034 A1 | 9/2006 | Stock et al. |
| 2006/0210120 A1 | 9/2006 | Rowe et al. |
| 2006/0253711 A1 | 11/2006 | Kallmann |
| 2007/0077176 A1 | 4/2007 | Lambert et al. |
| 2007/0142720 A1 | 6/2007 | Ridder et al. |
| 2007/0144812 A1 | 6/2007 | Stewart et al. |
| 2007/0245801 A1 | 10/2007 | Stock |
| 2008/0006077 A1 | 1/2008 | Crabtree et al. |
| 2008/0045806 A1 | 2/2008 | Keppler |
| 2008/0061238 A1 | 3/2008 | Hok et al. |
| 2008/0107309 A1 | 5/2008 | Carni |
| 2008/0171947 A1 | 7/2008 | Ruffert |
| 2008/0228098 A1 | 9/2008 | Popov et al. |
| 2008/0252412 A1 | 10/2008 | Larsson et al. |
| 2008/0319286 A1 | 12/2008 | Ridder et al. |
| 2009/0007634 A1 | 1/2009 | Mitchell |
| 2009/0039267 A1 | 2/2009 | Arndt et al. |
| 2009/0087920 A1* | 4/2009 | Pettersson ............ B60K 28/066 436/132 |
| 2009/0248260 A1 | 10/2009 | Flanagan |
| 2009/0293589 A1 | 12/2009 | Freund et al. |
| 2010/0010325 A1 | 1/2010 | Ridder et al. |
| 2010/0028210 A1 | 2/2010 | Ozaki et al. |
| 2010/0031718 A1 | 2/2010 | Heil |
| 2010/0036592 A1 | 2/2010 | Osaki et al. |
| 2010/0063409 A1 | 3/2010 | Hok |
| 2010/0188232 A1 | 7/2010 | Lambert et al. |
| 2010/0268425 A1 | 10/2010 | Pettersson et al. |
| 2010/0327167 A1 | 12/2010 | Koop et al. |
| 2011/0178420 A1 | 7/2011 | Ridder et al. |
| 2011/0283770 A1 | 11/2011 | Hok |
| 2011/0302992 A1 | 12/2011 | Robbins et al. |
| 2011/0308297 A1 | 12/2011 | Tsuzuki et al. |
| 2011/0309932 A1 | 12/2011 | Arrinqdale et al. |
| 2012/0112879 A1 | 5/2012 | Ekchian et al. |
| 2013/0110311 A1 | 5/2013 | Ver Steeg |
| 2013/0231871 A1 | 9/2013 | Hok |
| 2014/0002237 A1 | 1/2014 | Infante et al. |
| 2014/0156149 A1 | 6/2014 | Feit |
| 2014/0260537 A1 | 9/2014 | Nash |
| 2014/0297061 A1 | 10/2014 | Takahashi |
| 2014/0318293 A1 | 10/2014 | Nelson |
| 2014/0377877 A1* | 12/2014 | Burgi ............ G01N 33/4972 436/128 |
| 2015/0066238 A1 | 3/2015 | Todd et al. |
| 2015/0219620 A1 | 8/2015 | Hök et al. |
| 2015/0233897 A1 | 8/2015 | Hök |
| 2016/0356764 A1 | 12/2016 | Martin et al. |
| 2017/0050518 A1 | 2/2017 | Steeg et al. |
| 2017/0074857 A1* | 3/2017 | Dennis ............ A61B 5/4848 |
| 2017/0274768 A1 | 9/2017 | Hök et al. |

FOREIGN PATENT DOCUMENTS

| | | |
|---|---|---|
| CN | 101334399 A | 12/2008 |
| CN | 101624015 | 1/2010 |
| CN | 101631497 | 1/2010 |
| CN | 102316801 A | 1/2012 |
| CN | 102854303 | 1/2013 |
| CN | 104816692 | 8/2015 |
| DE | 4127599 A1 | 2/1993 |
| DE | 198 11 872 | 8/1999 |
| DE | 199 38 064 | 8/2000 |
| DE | 101 57 907 | 6/2003 |
| DE | 102006018970 B3 | 5/2007 |
| DE | 102011106410 | 8/2012 |
| EP | 0752584 | 1/1997 |
| EP | 0791899 | 8/1997 |
| EP | 1441212 | 7/2004 |
| EP | 1688741 | 8/2006 |

(56) References Cited

FOREIGN PATENT DOCUMENTS

| EP | 3304045 | 4/2008 |
|---|---|---|
| EP | 3433611 | 1/2019 |
| GB | 2431470 | 4/2007 |
| GB | 2442980 | 4/2008 |
| JP | 11-104112 | 4/1999 |
| JP | 2004-245799 | 9/2004 |
| JP | 2004-305494 | 11/2004 |
| JP | 2005-157599 | 6/2005 |
| JP | 2006-98058 | 4/2006 |
| JP | 2007-147592 | 6/2007 |
| JP | 2008-253455 | 10/2008 |
| JP | 2008-291710 | 12/2008 |
| JP | 2008-302915 | 12/2008 |
| JP | 2008-308037 | 12/2008 |
| JP | 2009-217633 | 9/2009 |
| JP | 2009-257768 | 11/2009 |
| JP | 2010-139319 | 6/2010 |
| JP | 2010-241369 | 10/2010 |
| JP | 2011-153956 | 8/2011 |
| JP | 2012-198648 | 10/2012 |
| JP | 2016-538193 | 12/2016 |
| KR | 20080110567 | 12/2008 |
| SE | 536782 | 8/2014 |
| SE | 536784 | 8/2014 |
| WO | WO 92/22813 | 12/1992 |
| WO | WO 95/26889 | 10/1995 |
| WO | WO 97/000443 | 1/1997 |
| WO | WO 98/20346 | 5/1998 |
| WO | WO 2001/008554 | 2/2001 |
| WO | WO 2004/090786 | 10/2004 |
| WO | WO 2007/046745 | 4/2007 |
| WO | WO 2008/108714 | 9/2008 |
| WO | WO 2009/048809 | 4/2009 |
| WO | WO 2010/085716 | 7/2010 |
| WO | WO 2010/093317 | 8/2010 |
| WO | WO 2012/064252 | 5/2012 |
| WO | WO 2013/081519 | 6/2013 |
| WO | WO 2014/031071 | 2/2014 |
| WO | WO 2014/031072 | 2/2014 |
| WO | WO 2016/195803 | 12/2016 |
| WO | WO 2017/164953 | 9/2017 |

OTHER PUBLICATIONS

Blincoe, L. J. et al., The Economic and Societal Impact Of Motor Vehicle Crashes, 2010 (Revised), National Highway Traffic Safety Administration, May 2015 (Revised), DOT HS 812 013.

Dhokalia et al., Resting End-Tidal $CO_2$ Association With Age, Gender, and Personailty, Psychosomatic Medicine, vol. 60, 1998, pp. 33-37.

Extended European Search Report EP 13 83 0956 dated Jul. 13, 2015.

Extended European Search Report EP 13 83 1692 dated Jul. 13, 2015.

Giebel, Brian M., Thesis and Dissertation, "Advancement and Application of Gas Chromatography Isotope Ratio Mass Spectrometry Techniques for Atmospheric Trace Gas Analysis," Published 2011, 252 total pages.

International Search Report dated Feb. 3, 2014 for PCT/SE2013/050991.

International Search Report dated Jan. 31, 2014 for PCT/SE2013/050990.

Lambert et al., Passive Sensing of Driver Intoxication, SAE Technical Paper 2006-01-1321, 2006, SAE International.

Talbert, Bruce, et al., "A Study of Regulators for Delivering Gases Containing Low Concentrations of Hydrogen Sulfide," LCGC North America, 22(6):562, 564, 567-568 (2004).

Traffic Safety Facts, 2013 Data: Alcohol-Impaired Driving, National Highway Traffic Safety Administration, Dec. 2014, DOT HS 812 102.

* cited by examiner

SENSOR SYSTEM FOR PASSIVE IN-VEHICLE BREATH ALCOHOL ESTIMATION

REFERENCE TO PENDING PRIOR PATENT APPLICATIONS

This patent application is a continuation of pending prior U.S. patent application Ser. No. 15/389,724, filed Dec. 23, 2016 by Automotive Coalition for Traffic Safety, Inc. for SENSOR SYSTEM FOR PASSIVE IN-VEHICLE BREATH ALCOHOL ESTIMATION, which patent application in turn claims benefit of prior U.S. Provisional Patent Application Ser. No. 62/312,476, filed Mar. 24, 2016 by Automotive Coalition for Traffic Safety, Inc. for SENSOR SYSTEM FOR PASSIVE IN-VEHICLE BREATH ALCOHOL ESTIMATION. The two (2) above-identified patent applications are hereby incorporated herein by reference.

STATEMENT REGARDING FEDERALLY SPONSORED RESEARCH OR DEVELOPMENT

This invention was made with Government support under contract number DTNH22-08-H-0188 awarded by the Department of Transportation National Highway Traffic Safety Administration. The government has certain rights in this invention.

FIELD OF THE INVENTION

This invention relates to methods for detection of breath alcohol concentrations in the exhaled breath of a driver, and particularly for rapid estimations of a driver's breath alcohol level.

BACKGROUND OF THE INVENTION

Supervised breath tests are regularly performed by police in an effort to prevent drunk driving. In addition to supervised breath tests, automated ignition interlock devices, sometimes called "alcolocks," that conduct unsupervised tests to prevent the operation of vehicles by drunk drivers, have been installed within vehicles themselves. Sensing technologies used for such breath tests may be based on catalytic beads (or pellistors), semiconductors, fuel cells or infrared spectroscopy. Typical breath test devices provide a signal representing Breath Alcohol Concentration (BrAC) after a driver has taken a deep breath and emptied his or her airways into a mouthpiece, which for hygienic reasons is often a separate, disposable item. To ensure a correct determination, the test person is required to deliver a forced expiration at almost full vital capacity. This requires substantial time and effort, especially for people with limited capacity. Ease of use, convenience, and accuracy are important factors for increasing the acceptance and adoption of built-in ignition interlock devices in vehicles.

SUMMARY OF THE INVENTION

There is therefore a need for a passive breath test that is flexible enough to avoid inconvenience to the driver while ensuring accuracy of the test under a wide range of environmental conditions and driver behaviors. In a passive breath test, the driver need not provide directed air to the sensor, and the BrAC measurement will be made, without additional action of the driver, from the air within the vehicle, which will be a mixture of breath of both the driver and any passengers, as well as ambient air. In contrast, in an active breath test, the driver may be required to be close to the sensor, and to direct a forced, undiluted breath towards the sensor or through an air inlet (e.g., blowing into a tube). While a passive breath test is preferred, under some conditions it may not be possible to perform an accurate passive breath test. Such conditions may be environmental (e.g., very hot weather) or the result of driver attempts to defeat the system (some examples are described below), but either way may result in the air within the vehicle not accurately reflecting the driver's BrAC. If normal testing conditions, under which an accurate passive BrAC test is possible, are not met, then an active breath test is required.

A variety of parameters indicating both environmental conditions and driver behavior are measured to detect when normal testing conditions are no longer met. These include, for example, detecting a peak in a tracer gas, which indicates that the driver's breath has been detected. A timer may set a time limit between when a driver's presence is detected and when a peak in the tracer gas is detected. This time limit may prevent driver attempts to defeat the system by holding his or her breath, or otherwise concealing his or her breath from the sensor. A pressure sensor may detect situations in which a driver has attempted to defeat the system by ventilating the vehicle, or in which wind that is blowing through the vehicle may prevent an accurate passive breath test. Detecting the driver's head position relative to a sensor may ensure that the driver's breath is being directed towards the sensor, in order to prevent attempts to defeat the system by supply an alternate source of "breath" to be measured.

The methods and apparatus described herein allow for passive detection of breath alcohol concentrations, and may be used for controlling ignition of a vehicle. In particular, the methods and apparatus are designed to determine BrAC from a passive breath test without inconveniencing the driver during normal testing conditions, detect when normal testing conditions no longer are met, and provide for BrAC measurement from an active breath test under those circumstances.

In an example of a method or apparatus for passive breath alcohol detection for operating a vehicle, the apparatus may include sensors which measure the concentration of a tracer gas in a passively obtained first air sample, while the method may include initiating the sensor system, passively obtaining a first air sample, and measuring the concentration from the first air sample. The apparatus may include a processor, which determines, using the sensor system, a set of testing conditions based in part on the first air sample, while the method may include that determining. If the set of testing conditions is within a normal range and a peak in tracer gas concentration is detected, the method or processor measures a BrAC of a driver from the first air sample. If the set of testing conditions is outside of the normal range or no peak in tracer gas concentration is detected, the method or processor requests an active second air sample from the driver and measures the BrAC of the driver.

In some embodiments, the method includes measuring a time interval between initiating the sensor system and detecting the peak in tracer gas concentration. In some embodiments, the apparatus includes a timer which measures that time interval. If the time interval exceeds a predetermined time limit, the method or processor determines that the set of testing conditions is outside of the normal range. In some embodiments, the apparatus includes sensors which measure the environmental conditions of the vehicle, and in some embodiments the method includes measuring such environmental conditions. In some embodiments, such a sensor may be a temperature sensor, and in some embodiments the method includes measuring the temperature within the vehicle. If the temperature is outside a normal temperature range, the method or processor determines that the set of testing conditions is outside of the normal range. In some embodiments, the apparatus includes a pressure sensor to measure the pressure within the vehicle, and in some embodiments the method includes measuring that pressure. If the pressure is outside a normal pressure range, the method or processor determines that the set of testing conditions is outside of the normal range. In some embodiments, the apparatus includes a camera which measures the driver's head position relative to a BrAC sensor, and in some embodiments the method includes measuring the driver's head position relative to a BrAC sensor. In some embodiments, initiating the sensor system includes detecting the presence of the driver entering the vehicle. In some embodiments, measuring the BrAC of the driver from an active breath test includes determining if a measured BrAC from a passive breath test is at an intermediate level. If the measured BrAC is at the intermediate level, the method requests an active breath sample and measures BrAC. In some embodiments measuring the BrAC of the driver from an active breath test includes requesting, through a Human-Machine Interface (HMI), an undiluted breath sample directed towards the BrAC sensor.

In some embodiments, the method includes sending sensor signals to a central processing unit (CPU) of the breath test system, which is in communication with a CPU of the vehicle. In some embodiments, the processor receives the sensor signals from the sensors. In some embodiments, the method includes disabling the operation of the vehicle if the result of the driver's BrAC measurement is above a set point, which may also be done with a processor. In some embodiments, the method includes enabling the operation of the vehicle if the result of the driver's BrAC is below a set point, which may also be done with a processor. In some embodiments, the method includes requesting an active second air sample from the driver and measuring the BrAC of the driver if the result of a passive breath test of a first air sample is at an intermediate level. In some embodiments, the request may be made by a processor. In some embodiments, the method includes continuously measuring air samples after initiating the sensor system, and continuously measuring the concentration of the tracer gas after the first air sample is measured. In some embodiments, the sensors continuously measure air samples after initiating the sensor system, and also continuously measure the concentration of the tracer gas after the first air sample is measured.

BRIEF DESCRIPTION OF THE DRAWINGS

Further features of the subject matter of this invention, its nature and various advantages, will be apparent upon consideration of the following detailed description, taken in conjunction with the accompanying drawings, in which like reference characters refer to like parts throughout, and in which.

DETAILED DESCRIPTION

Figure 1:
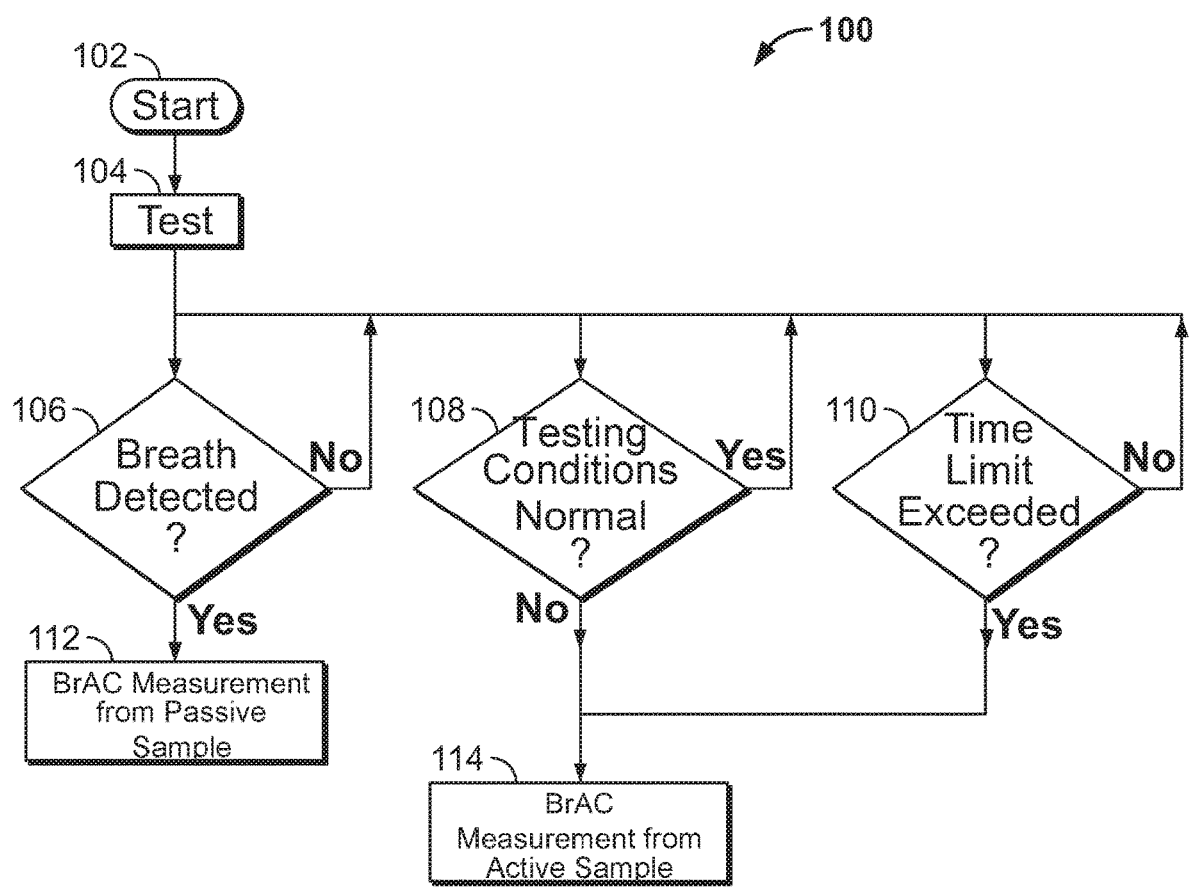
FIG. 1 depicts a flowchart of a process for determining a BrAC measurement from passive or active breath samples, according to an illustrative implementation.

Administering breath tests to drivers is an effective screening method to reduce drunk driving and drunk driving related deaths. In breath testing, a subject exhales air into a sensor or measuring device for a sufficient time and of a sufficient volume to achieve breath flow that originates from the alveoli of the lungs, where substances such as ethyl alcohol (EtOH) in the blood are exchanged with air. The sensor or measuring device then measures the alcohol content in the air, which is related to blood alcohol through a conversion algorithm.

Existing breath based alcohol testing technologies require the driver to deliver a forced expiration at almost full vital capacity. This requires substantial time and effort, especially for people with limited lung capacity. For hygienic reasons, the mouthpiece used in existing breath testing devices may also need to be cleaned and replaced after multiple uses. Additionally, environmental conditions, such as wind, temperature, the presence of other people, etc. may significantly affect the accuracy of a BrAC measurement. To improve the adoption and public acceptance of ignition interlock devices in vehicles, a breath testing system that does not inconvenience the driver and is robust under the wide range of conditions found in a vehicle is needed.

There is therefore a need for a passive breath test that is flexible enough to avoid inconveniencing the driver while ensuring accuracy of the test under a wide range of environmental conditions and driver behaviors. In a passive breath test, the driver need not provide directed air to the sensor, and the BrAC measurement will be made, without additional action of the driver, from the air within the vehicle, which will be a mixture of breath of both the driver and any passengers, as well as ambient air. In passive breath testing, the air within the vehicle is pulled into the sensor with a fan. The BrAC measurement is made by first measuring the concentration of a tracer gas, such as carbon dioxide, which indicates the dilution of the driver's breath in the air within the vehicle. Then the measured EtOH concentration can be combined with this breath dilution factor to determine a BrAC. The BrAC measurement is thus made without inconvenience to the driver simply through sampling the air within the vehicle.

In contrast, in an active breath test, the driver may be required to be close to the sensor, and to direct a forced, undiluted breath towards the sensor or through an air inlet (e.g., blowing through a tube). In the active breath test, BrAC is thus measured directly from the driver's breath, rather than through the air within the vehicle. The active breath test requires action by the driver separate from the normal actions required to start the vehicle and may thus be considered more inconvenient than the passive breath test.

While a passive breath test is preferred, under some conditions it may not be possible to perform an accurate passive breath test. For example, the driver may attempt to defeat the system, resulting in the air within the vehicle not accurately reflecting the driver's BrAC. Similarly, environmental conditions within the vehicle (such as high wind from open windows, or high temperatures after the vehicle has been standing closed in hot weather) may not allow for accurate BrAC measurement. If normal testing conditions, under which an accurate passive BrAC test is possible, are not met, then an active breath test will be required of the driver.

The present invention provides a variety of sensing checks to allow for passive detection and estimation of a driver's BrAC under normal conditions, while switching to BrAC measurement from an active breath test when normal conditions are no longer met. This reduces driver inconvenience by defaulting to a passive estimation of BrAC, while simultaneously providing alternative logic pathways when the accuracy of a BrAC estimation is non-definitive, the driver behavior or testing conditions are outside of a norm.

FIG. 1 depicts a flowchart of a process for determining BrAC measurement from passive or active breath samples, according to an illustrative implementation. The process 100 starts at 102. Start 102 may be initiated by a wireless door key to unlock the vehicle doors, by opening the door to the driver's seat, or any other indicator capable of signaling that a driver has entered a vehicle. As the driver or test subject takes the first steps towards entering the driver seat of the vehicle, process 100 will initiate sensors to monitor the testing conditions within the vehicle, the detection of a driver's breath, and to begin a timer to check whether a driver's breath has been detected within a time limit during testing at 104. If a driver's breath is detected (as determined at logic gate 106), the testing conditions within the vehicle are normal (as determined at logic gate 108), and the time limit has not been exceeded (as determined at logic gate 110), then the process 100 will proceed to 112 and a BrAC measurement from a passive breath sample will be made. However, if either of the logic gates 106 or 108 make a negative determination, or a time limit has been exceeded at 110, then process 100 will proceed to request from the driver an active breath sample at 114.

The testing at 104 includes a self-test of all function blocks and sensors used in the process 100. At testing 104, stable operating temperatures of temperature-sensitive elements of any sensors used in process 100 are established. This may include, for example, the heating of mirrors within a tracer gas detection sensor above 40° C. The mirrors and tracer gas detection sensor are described in further detail with reference to FIG. 4. The self-test procedure conducted 104 may last between 5-8 seconds in testing conditions at or above room temperature. The self-test procedure may last longer than 8 seconds at low temperatures. The testing at 104 may also entail measuring the initial conditions of the vehicle before the driver has entered, such as $CO_2$ levels, EtOH concentrations in the vehicle air, air temperature, air pressure, etc. These initial conditions may be used to determine, at logic gates 106 and 108, if driver breath has been detected and if the testing conditions are within normal ranges, respectively.

A tracer gas may be any gas used to detect the driver's breath. The tracer gas may be carbon dioxide ($CO_2$) or any other gas that may indicate exhaled breath. The sensitivity of a tracer gas detection sensor allows for detection of highly diluted exhaled breath, which may have a dilution factor (i.e. ratio between ambient air and undiluted breath) greater than or equal to 50. Air is continuously drawn through the tracer gas detection sensor from the air within the vehicle following initiation of the process 100. The tracer gas detection sensor may be located closer to the position of the driver's head than any passenger position, e. g. at the steering column or side door nearest the driver's side of a vehicle. Exhaled breath is recognized as a signal peak output by the tracer gas detection sensor. If the tracer gas is $CO_2$, the baseline concentration of $CO_2$ corresponding to the baseline signal is expected to be between 400 and 600 ppm (0.04%-0.06% volume). Tracer gas signals and initiation signals for 102 are described in further detail with reference to FIG. 6. The tracer gas detection sensor, which determines if breath is detected at logic gate 106, is described in further detail with reference to FIG. 4. The breath sample in which the tracer gas detection peak is found may be the same breath sample used for the BrAC measurement at 112. Thus detecting a driver's breath during testing 104 and the logic gate 106 may occur approximately simultaneously to the BrAC measurement from a passive breath sample made at 112.

Logic gate 108 may process the testing conditions of a vehicle and determine if they are within normal conditions capable of producing an accurate BrAC measurement from a passive breath sample. Environmental conditions may entail both the behavior of the driver and the state of the vehicle itself. These conditions may be detected by a variety of sensors, including the tracer gas detection sensor, as well as auxiliary sensors placed throughout the vehicle. Sensors may include temperature sensors to determine temperature within the vehicle, pressure sensors to determine the barometric pressure within the vehicle as well as wind or air through the interior of the vehicle. Normal temperatures within a vehicle may be within a range of −40° C. to 85° C. This may be the temperature range over which a BrAC sensor can take accurate passive breath tests. Normal barometric pressure may be within a range of 80 to 105 kPa. This may be the pressure range over which mixing of the driver's breath with ambient air can produce accurate passive breath tests. Temperature and pressure sensors may be any standard sensor element and may be embedded in the body of the vehicle.

A camera sensor to monitor driver behavior may also be placed near the driver, such as close to a steering wheel column. This camera sensor may detect the position of a driver's head with respect to the tracer gas detection sensor, as described in further detail with respect to FIG. 5. The relation between the driver's head and the tracer gas detection sensor may determine if the driver is breathing in the direction of the tracer gas detection sensor. The camera may detect scenarios in which the driver is attempting to avoid detection of his or her BrAC by facing away from the sensor. The camera sensor may also detect the presence of unfamiliar objects near the driver's face, such as a mask, filter, spray bottle, or other object meant to interfere with the tracer gas detection sensor, or to supply an alternate source of "breath" to prevent an accurate passive breath test. The camera sensor may also detect the close-by position of passengers, which may make it difficult to distinguish between the passenger's BrAC level and the driver's BrAC level, or where the driver is attempting to have the system measure the passenger's BrAC level rather than his or her own BrAC level. Logic gate 108 may also determine the status of a vehicle's heating, ventilation and air conditioning (HVAC) system, such as whether it is in an ON state or an OFF state. The HVAC system is preferably turned OFF or in a normal operating condition during the process 100. Use of the HVAC system during passive breath testing may excessively dilute the driver's EtOH level, divert the driver's breath away from the sensor, or otherwise prevent an accurate passive breath test. Logic gate 108 may also detect the presence of windshield fluid. Windshield fluid typically includes ethyl alcohol, which may influence the detection of EtOH within the vehicle. The windshield fluid is in an OFF state in normal testing conditions. Logic gate 108 may determine the states of both the vehicle's HVAC system and the state of the windshield fluid through communication with the vehicle, such as with the vehicle's CPU or Controller Area Network (CAN) bus.

The logic gate at 110 determines if a time limit has been exceeded for process 100 to detect the breath of a driver during test 104. This may be a predetermined time limit, such as from 10 to 30 seconds. If, at 110, it is determined that this time limit has been exceeded, then the process 100 proceeds to a BrAC measurement from an active breath sample at 114. The time limit may prevent situations in which a driver is avoiding breathing in the direction of the sensor, holding his or her breath, has placed a mask over his or her head, or is otherwise attempting to operate a vehicle without providing a breath sample. In this case, the logic gate at 110 will recognize that a breath has not been detected after the predetermined time limit, and will require an active breath sample from the driver at 114.

If, at logic gate 106, the exhaled breath of a driver is detected, while logic gate 108 has determined that testing conditions are normal and logic gate 110 has determined that a time limit has not been exceeded, then process 100 will proceed to a measure BrAC from a passive breath sample at 112. BrAC measurement 112 may be described in further detail with reference to FIG. 2. If, however, breath is not detected at 106, then process 100 will continue to test for the breath of the driver until either a time limit is exceeded at 110 or unless normal testing conditions are not met at 108. In this case, process 100 will require an active breath sample at 114 from which BrAC is measured. The determination at 108 that normal testing conditions have not been met is sufficient to require an active breath sample at 114. Similarly, if at 110 it is determined that a time limit has been exceeded, process 100 will proceed to an active breath sample at 114. The active breath sample at 114 may be described in further detail with reference to FIG. 3. The results of BrAC measurements 112 and 114 may differ in accuracy.

Figure 2:
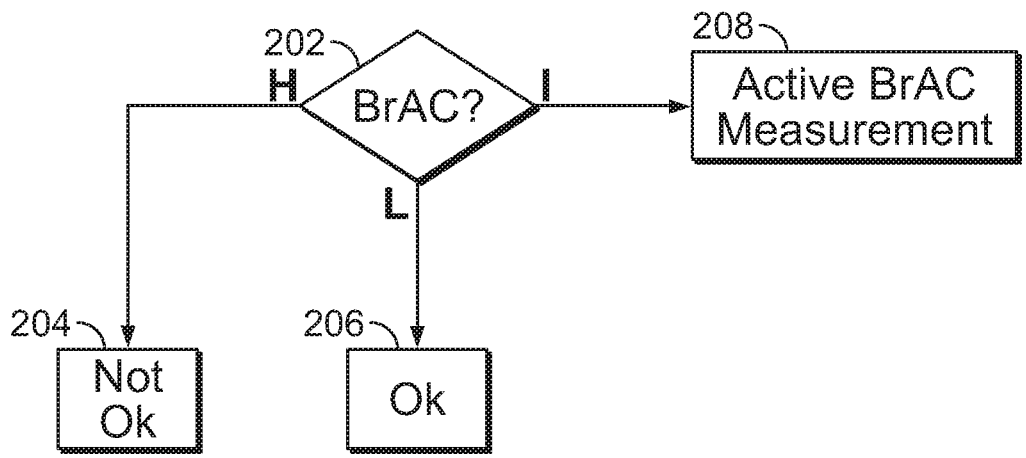
FIG. 2 depicts a flowchart of a process for determining the outcome of a BrAC measurement from a passive breath sample, according to an illustrative implementation.

FIG. 2 depicts a flowchart of a process for determining the outcome of a BrAC measurement from a passive breath sample, according to an illustrative implementation. Process 112 determines a driver's BrAC at 202. Process 112 may be approximately simultaneous to the detection of a tracer gas at 104 and 106, as shown in FIG. 1. Process 112 may thus be carried out using the same breath sample collected at 104 to detect a peak in tracer gas indicating the breath of a driver. The measurement of BrAC is based on the dilution of a detected tracer gas, which may be $CO_2$. The detected dilution factor, or DF, of the tracer gas in the vehicle's ambient air is used to determine an estimate of the driver's BrAC. The BrAC level may be determined according to the following equation:

$$BrAC = EtOH * DF \qquad (1)$$

Figure 3:
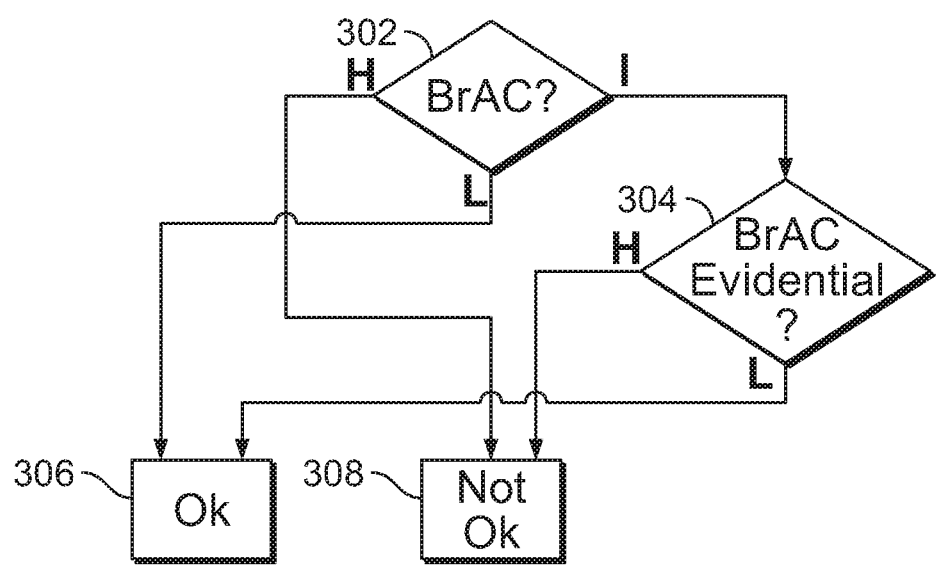
FIG. 3 depicts a flowchart of a process for determining the outcome of a BrAC measurement from an active breath sample, according to an illustrative implementation.

DF is the dilution factor of the tracer gas in air. Additional algorithms may be used incorporating information from auxiliary sensors (not shown). The algorithm used measure BrAC from a passive breath sample at 112 may be different from the algorithm used to measure BrAC from an active breath sample at 114. If the estimated value of BrAC is below a predetermined set point (denoted "Low" or "L") then the process 112 outputs a signal at 206 that the BrAC of a driver is "OK." The predetermined set point may be in the interval of 0.1 to 0.4 mg/L (50 to 200 ppm). The predetermined set point may be a function of the driver's age. The predetermined set point may be a function of a legal limit on blood alcohol concentration for driving under the influence (DUI) or driving while impaired (DWI). Signal 206 may be used to enable the operation of a vehicle. If the estimated BrAC value is well above the predetermined set point (denoted "High" or "H"), then the process 112 will output a signal at 204 indicating that the BrAC of a driver is "Not OK." A BrAC level of 0.1-0.2 mg/L (50 to 100 ppm) above said set point may cause the output of the signal at 204 indicating that the BrAC of the driver is "Not Ok." Signal 204 may be used to disable the operation of a vehicle. If, at 202, it is determined that the BrAC of a driver is within an intermediate range (denoted "Intermediate" or "I") slightly above or below the predetermined set-point, then further analysis of the driver's breath is required to make a final determination. The driver is then asked to perform an active breath test at 208. The active breath test is described in further detail with reference to FIG. 3, and is the process 114 as shown in FIG. 1 and FIG. 3. A sensor, such as the sensor described in FIG. 4 may make the measurement at 202, while external processing such as described in further detail in FIG. 4 may communicate the signals 204 and 206 to a central processing unit, or CPU 415.

FIG. 3 depicts a flowchart of a process for determining the outcome of an BrAC measurement from an active breath sample, according to an illustrative implementation. Process 114 begins at 302 where the BrAC of a driver is measured. In the aBrAC measurement from an active breath sample at 302, a driver is requested to provide an active breath towards a sensor (not shown) at a distance of 15-30 cm from the sensor. The distance may be adjusted for the location of the sensor within the vehicle. If the BrAC is below a predetermined set point (denoted "Low" or "L") then the process 114 outputs a signal at 306 that the BrAC of a driver is "OK." Signal 306 may be used to enable the operation of a vehicle. If the estimated BrAC value is well above the predetermined set point (denoted "High" or "H"), then the process 114 will output a signal at 308 indicating that the BrAC of a driver is "Not OK." Signal 308 may be used to disable the operation of a vehicle. If, at 302, it is determined that the BrAC of a driver is within an intermediate range (denoted "Intermediate" or "I") slightly above or below the predetermined set-point, then the driver will be requested to provide a breath sample with evidential accuracy at 304. The breath test performed at 304 will require an undiluted breath sample. From test 304 there is no intermediate response. The breath test at 304 will require the driver to direct an active breath towards a sensor (not shown) at a distance of 15-30 cm from the sensor. The distance may be adjusted for the location of the sensor within the vehicle. If the measured BrAC value is below a set-point (L) then process 114 will produce an output signal at 306 indicating that the BrAC of a driver is "OK." If the measured BrAC value is above a set-point (H) then the process 114 will produce an output signal at 308 indicating that the BrAC of a driver is "Not OK."

The logic gates 106, 108, 110 in FIG. 1, 202 in FIG. 2, and 302 and 304 in FIG. 3 are shown as representing "IF . . . THEN" logical statements, however these logic gates are not restricted to elements of Boolean logic. Logic gates 106, 108, 110, 202, 302 and 304 may also demonstrate fuzzy logic or be governed by artificial neural networks. The desired logic system may be programmed into a CPU 415 as described in further detail with reference to FIG. 4.

Figure 4:
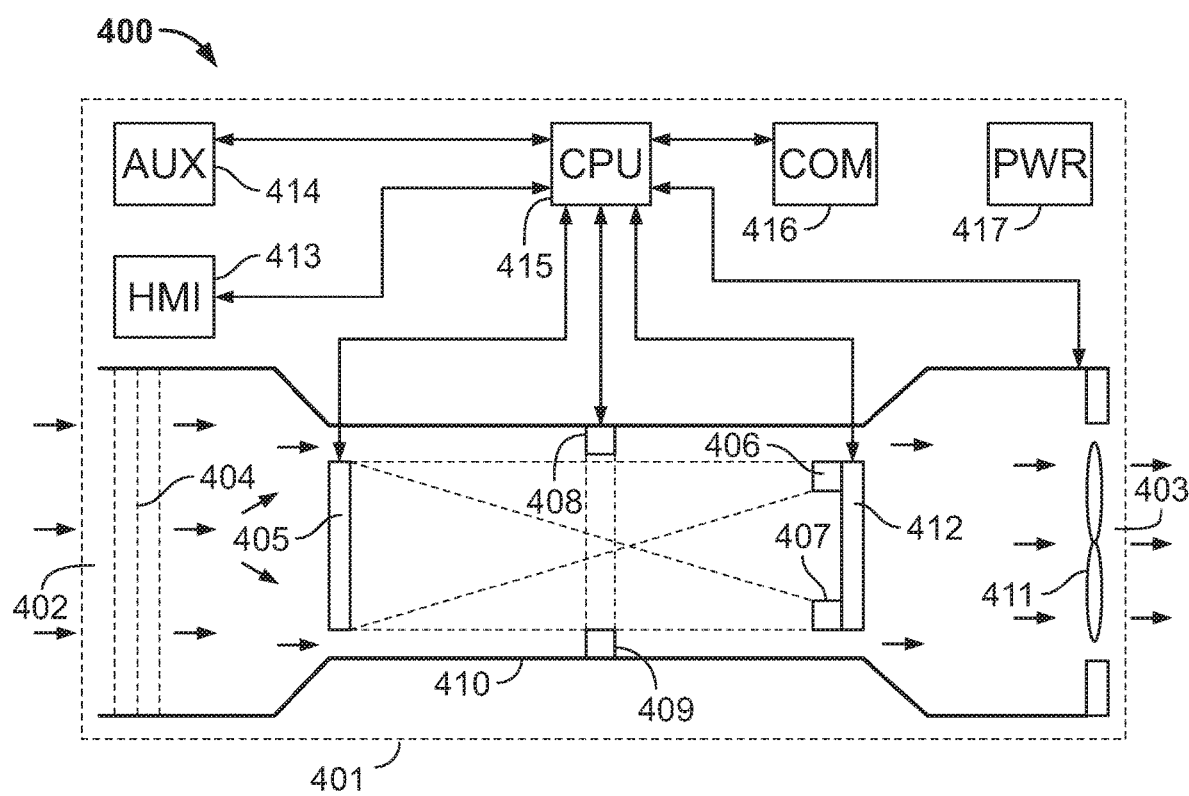
FIG. 4 depicts a sensor for detecting breath and BrAC concentrations from both active and passive breath samples, according to an illustrative implementation.

FIG. 4 depicts a sensor for detecting breath and BrAC concentrations from both active and passive breath samples, according to an illustrative implementation. The sensor 400 may detect breath during test 104 as shown in FIG. 1, measure initial conditions of the vehicle at 104, as well as perform both the BrAC measurement from a passive breath sample 112 and the BrAC measurement from an active breath sample 114 as shown in FIG. 1, and described in further detail with reference to FIG. 2 and FIG. 3. The sensor 400 draws air continuously through an inlet 402, to an outlet 403, and measures for both the presence of a tracer gas such as $CO_2$ and the presence of EtOH within the airflow. The sensor 400 determines whether a driver's BrAC is within a Low, High or Intermediate range, as described with reference to FIG. 2 and FIG. 3.

The sensor 400 is contained within an enclosure 401, and may be a stand-alone sensor or designed for integration into the interior of a vehicle, such as within a steering wheel column, a side door, A- or B-vertical support pillars, a sun visor, dashboard, or other convenient position significantly closer to a driver's head than to a passenger-designated area of the vehicle. The enclosure 401 may be airtight except for the openings at the sensor input 402 and outlet 403. The enclosure 401 may have the approximate dimensions of 25×40×120 mm. The air brought into the enclosure 401 through the inlet 402 is heated to above body temperature by an inlet heater 404, which may avoid condensation at low ambient temperatures. The inlet heater 404 may have a large surface contact area to the inlet air in order to improve heat transfer from the heater to the incoming air. The heater 404 may be a resistive heater. The air flow from the inlet 402 to the outlet 403 is driven by a fan 411 located close to the outlet 403.

The sensor 400 measures the presence of both $CO_2$ and EtOH through infrared (IR) spectroscopy. IR spectroscopy uses the specific "fingerprint" that gas-phase alcohol produces when illuminated by infrared light to determine an alcohol concentration within the airflow of the sensor 400. The detected absorption spectrum of any substance is a product of resonant molecular vibrations, which are specific to the atomic bonds within a molecule or compound in the breath sample. From the absorption spectrum, particular substances and their absolute or relative concentrations within the breath sample can be determined.

To perform IR spectroscopy and detect both the presence of a tracer gas and the presence of EtOH, the sensor air chamber tube 410 includes two separate optical paths, one for detection of a tracer gas and a second for detection of EtOH. The signals produced by these two optical paths are used to determine the value of a dilution factor of the driver's breath in ambient air (or DF as shown in Equation 1) as well as the value of EtOH concentration within the input air.

The first optical pathway, composed of an EtOH IR emitter 406 and EtOH IR detector 407 as shown in FIG. 4 will determine an EtOH concentration. The EtOH IR emitter 406 outputs IR radiation into the interior of the sensor air chamber tube 410. A spherical mirror assembly composed of a first mirror 405 placed at one end of the air chamber tube 410 and a second mirror 412 located at the opposite end of the air chamber tube 410 reflects the emitted IR radiation from the EtOH IR emitter 406. The optical path length of the emitted IR radiation may be several times that of the distance between the first mirror 405 and the second mirror 412, as the mirror assembly will reflect the emitted light several times before it hits the EtOH IR detector 407. The optical path is shown as dashed lines in FIG. 4, however this is shown as an example and the actual optical path between the EtOH IR emitter 406 and the EtOH IR detector 407 may be much longer.

The EtOH IR emitter 406 may be a black-body radiator, IR laser diode, or any other optical source capable of producing IR light and preferably with a small mass to fit within the air chamber tube 410. The EtOH IR emitter 406 may be modulated at a frequency between 5-10 Hz in order to suppress low frequency noise and disturbances in the signal of the EtOH IR detector 407. The EtOH IR detector 407 includes a bandpass filter that is tuned to the IR absorption peak for EtOH, which is approximately 9.5 µm. The EtOH IR detector 407 may be a pyroelectric or photonic detector, capable of producing a high resolution signal, and may also include a Peltier element for localized cooling in order to suppress thermal noise in the detection signal. The detection signal produced by the EtOH IR detector 407 is described in further detail with reference to FIG. 6. The sensor 400 is specifically designed for high resolution IR spectroscopy measurements, and may have a resolution exceeding 0.5 µg/L (or 1.2 ppm) of EtOH, enabling the estimation of alcohol concentration in highly diluted breath.

The second optical pathway is dedicated to detecting the presence of a tracer gas, such as $CO_2$, which will indicate the dilution of a driver's breath within the air input through the sensor 400. A tracer gas IR emitter 408 is placed opposite a tracer gas IR detector 409 such that the optical path from the tracer gas IR emitter 408 to the tracer gas IR detector 409 is across the shorter dimension of the air chamber tube 410. The tracer gas IR detector 409 may be tuned to a wavelength band specific to the IR absorption frequency of the detected tracer gas. In an example where the tracer gas is $CO_2$, the absorption peak may be at 4.26 µm. Due to the high end tidal concentration of $CO_2$ in exhaled air, which is typically at 4.2% volume, a short optical path across the air chamber tube 410 may be used. This path is indicated in FIG. 4 as a dashed line between the tracer gas IR emitter 408 and the tracer gas IR detector 409. The signal produced by the tracer gas IR detector is described in further detail with reference to FIG. 6.

The signals from both EtOH IR detector 407 and tracer gas IR detector 409 may be used to determine if normal conditions for the passive measurement of BrAC are met, such as during the test 104 and the logic gate 108 of process 100 as shown in FIG. 1. This may entail checking that the baseline presence of the tracer gas is within standard levels, such as the baseline concentration of $CO_2$ in ambient air.

The first mirror 405 and the second mirror 412 are both in communication with a central processing unit, or CPU 415 as shown in FIG. 4. The EtOH IR emitter 406, EtOH IR detector 407, tracer gas IR emitter 408 and tracer gas IR detector 409 may also be in signal communication with the CPU 415. CPU 415 processes the signal generated by the EtOH IR detector 407 and the tracer gas IR detector 409 to determine BrAC measurements.

An HMI 413 is in communication with the CPU 415 and may be used to communicate with a driver to request an BrAC measurement from an active breath sample. The HMI 413 includes audiovisual means for communication with a driver, such as a screen and speakers to convey messages and a request for an active breath test, as well as other directions to a driver. The HMI may display the result of a BrAC measurement to the driver. The HMI may be a multi-purpose interface, such that requesting and displaying information related to a breath test is only one of many functions. Other functions may be navigation, HVAC interaction, stereo system interaction, or other system interactions typical for a vehicle. The HMI may be integrated into the vehicle within view of the driver.

The CPU 415 is also in communication with auxiliary sensors 414, which may be, for example, temperature, barometric pressure or optical sensors, or a camera to determine the testing conditions within a vehicle. The auxiliary sensors 414 are used during the test 104 of process 100. A data communication unit 416 may store parameter values used by the CPU to determine BrAC measurements and normal testing conditions of the vehicle. The data communication unit 416 also transfers data between the sensor system 400 and other units outside of the sensor 400 (not shown). The sensor 400 also includes a power unit 117 for power management and supply.

Figure 5A:
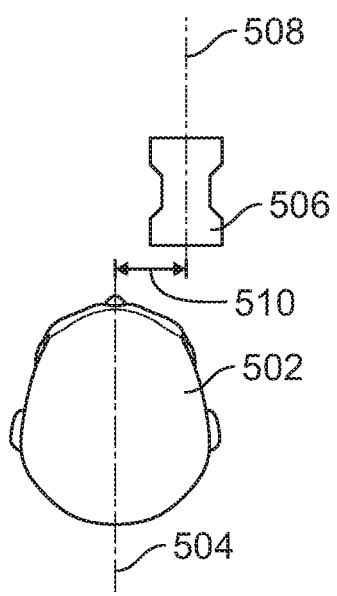
FIGS. 5A and 5B are an overhead view of a driver's head position in relation to a sensor, according to an illustrative implementation.

FIG. 5 is an overhead view of a driver's head position in relation to a sensor, according to an illustrative implementation. Auxiliary sensors measure a lateral distance 510 between the driver 504 and the sensor 506. The lateral distance 510 may be measured between the midline of the sensor 508 and the midline of the driver's head 504. Under normal testing conditions, the lateral distance 510 is less than or equal to 20 cm. The measurement of lateral distance 510 may occur at the test 104 of process 100 as shown in FIG. 1. The determination at logic gate 108 if the testing conditions of the vehicle are normal takes into account the lateral distance 510 as shown in FIG. 5A. Measurement of the lateral distance 510 may ensure that the driver is breathing directly towards the sensor 506 during an active breath test. Measurement of lateral distance 510 may also ensure that during passive breath testing, the driver is not attempting to avoid breath detection of the sensor by holding his or her head away from the direction of the sensor.

Figure 5B:
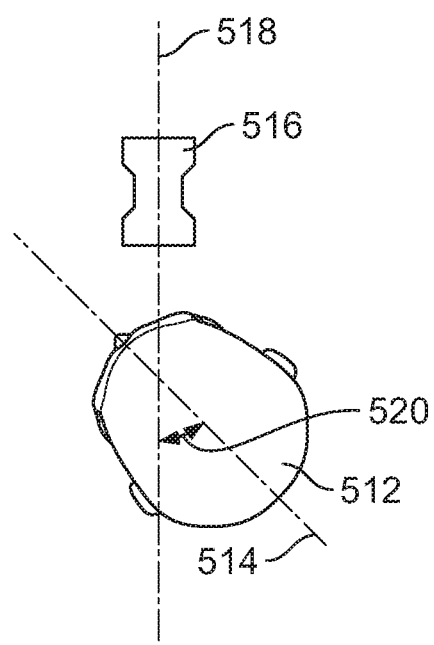

Auxiliary sensors also measure a driver's head rotation in relation to the midline 518 of sensor 516. The rotational angle 520 may be measured between the midline 518 of the sensor 516 and the midline 514 of the driver's head 512. Under normal testing conditions, the rotational angle 520 may be ±5°. The measurement of the rotational angle 520 may occur at the test 104 of process 100 as shown in FIG. 1. The determination at logic gate 108 of whether or not testing conditions of the vehicle are normal takes into account the rotational angle 520 as shown in FIG. 5B. Measurement of the rotational angle 520 may ensure that the driver is breathing directly towards the sensor 516 during an active breath test. Measurement of the rotational angle 520 may also ensure that during passive breath testing, the driver is not attempting to avoid breath detection of the sensor by holding his or her head away from the direction of the sensor.

The lateral distance 510 and rotational angle 520 may be measured by an embedded camera sensor (not shown), which may be incorporated into a vehicle and placed near a driver's head. The embedded camera may also determine if there is an unfamiliar object within the camera's field of view, and/or whether a passenger is within field of view of a driver's head.

Figure 6:
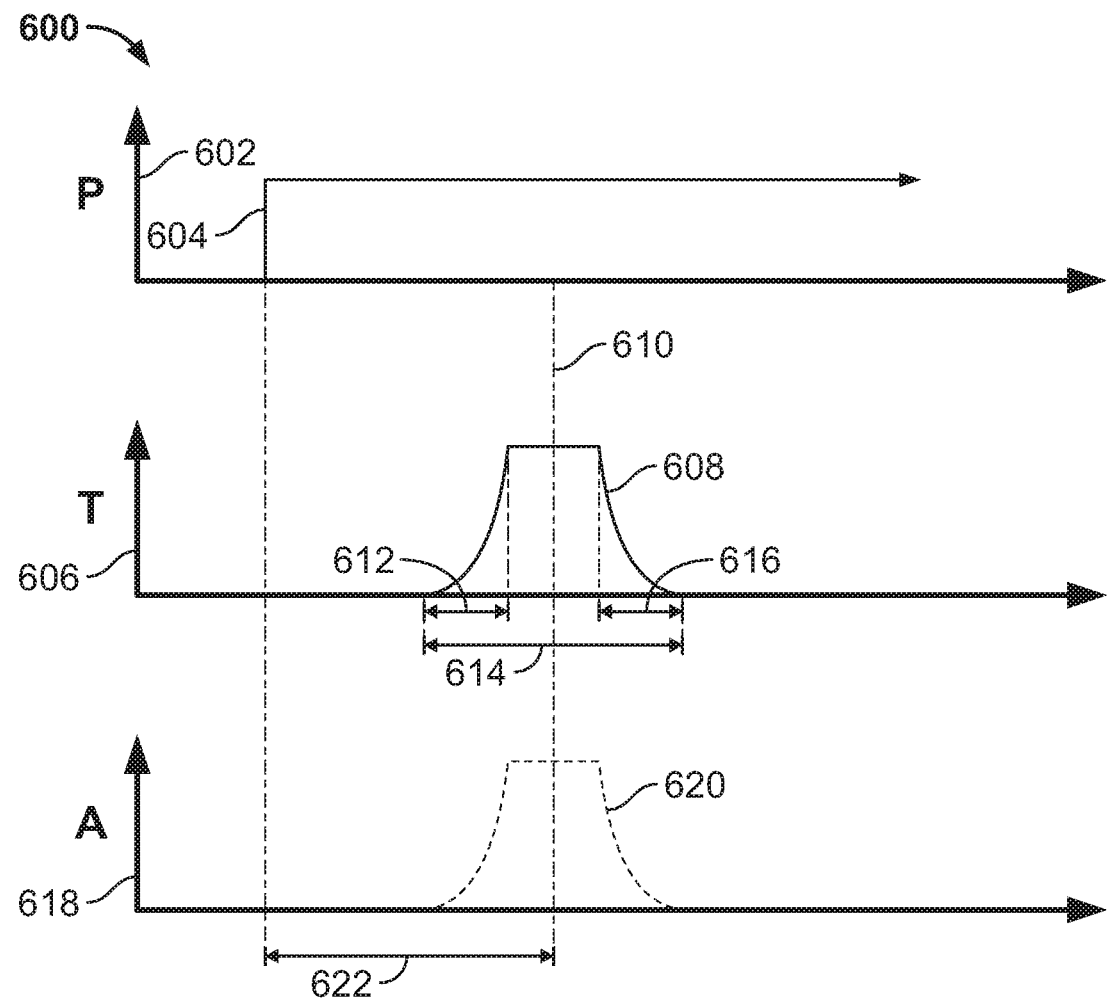
FIG. 6 is a graph representing examples of signals detected by an initiation sensor and a BrAC sensor, according to an illustrative implementation.

FIG. 6 is a graph representing examples of signals detected by an initiation sensor and BrAC sensor, according to an illustrative implementation. The graphs shown at 600 occur along the same time scale. Graph 602 (denoted "P") shows a signal 604 representing the detection of the presence of a driver as he or she enters or prepares to enter a vehicle. Signal 604 initiates the start 102 as shown in process 100 in FIG. 1. Signal 604 begins a timer that will determine the time interval between the initiation signal at 604 and the detection of a breath, which is shown at graph 606 (denoted "T"). Breath is detected from a peak 608 in the concentration of a tracer gas signal. When the tracer gas is $CO_2$, a peak in breath detection is characterized by a magnitude of $CO_2$ detection at or above 525 ppm, assuming a dilution factor of 80, and assuming an end-tidal $CO_2$ concentration of 4.2% volume. The duration of the peak 614 is expected to be 1-3 seconds, excluding the response time of the sensor. The rise time of the peak 612 as well as the decline time 616 may also be used to characterize the tracer gas signal as the result of exhaled breath of a driver. Typical rise times may be in the range 0.5 to 1.0 seconds, while typical decline times may be in the range 3 to 5 seconds. The peak in the tracer gas signal at 610 may end the timer. The time interval 622 may be measured and used to determine if an acceptable time limit has been exceeded between the initiation signal 604 and the breath signal 608, such as at logic gate 110 as shown in FIG. 1.

Graph 618 shows the detection signal for EtOH. Depending on the concentration of EtOH within a driver's breath, graph 618 may or may not show a peak 620 corresponding to the peak 608 in the tracer gas. If, however, there is EtOH in the driver's breath, the EtOH signal 620 will be approximately simultaneous to the tracer gas signal 608, as shown in FIG. 6. The magnitude of the peak will indicate the concentration of BrAC in the measured breath sample. Measurement of BrAC from peak 620 may occur approximately simultaneously to the detection of peak 608.

It will be understood that the foregoing is only illustrative of the principles of the invention, and that the invention can be practiced by other than the described embodiments, which are presented for purposes of illustration and not of limitation, and the present invention is limited only by the claims which follow.

What is claimed is:

1. A method for passive breath alcohol detection for vehicle operation, the method comprising:
   initiating a sensor system;
   passively obtaining a first air sample of air in a vehicle;
   measuring a concentration of a tracer gas in the first air sample;
   monitoring, using the sensor system, at least one testing condition affecting the ambient air inside the vehicle;
   determining if the at least one testing condition is within a predefined range;
   if the at least one testing condition is within the predefined range and a peak in tracer gas concentration is detected, measuring a Breath Alcohol Concentration (BrAC) from the first air sample;
   if the at least one testing condition is outside of the predefined range, requesting and actively obtaining a second air sample from a driver of the vehicle and measuring the BrAC of the driver.

2. The method of claim 1, further comprising:
   measuring a time interval between initiating the sensor system and detecting the peak in tracer gas concentration; and
   if the time interval exceeds a predetermined time limit, determining that the at least one testing condition is outside of the predefined range.

3. The method of claim 2, wherein the at least one testing condition comprises:
   measuring the environmental conditions of a vehicle.

4. The method of claim 3, wherein measuring the environmental conditions of the vehicle comprises:
   measuring a temperature within the vehicle; and
   if the temperature is outside a predetermined temperature range, determining that the at least one testing condition is outside of the predefined range.

5. The method of claim 3, wherein measuring the environmental conditions of the vehicle comprises:

measuring a pressure within the vehicle; and
if the pressure is outside a predetermined pressure range, determining that the at least one testing condition is outside of the predefined range.

6. The method of claim 1, further comprising measuring the driver's head position relative to a BrAC.

7. The method of claim 1, further comprising detecting the presence of the driver entering the vehicle.

8. The method of claim 1, wherein requesting and actively obtaining the second air sample from the driver and measuring the BrAC of the driver further comprises:
determining if a measured BrAC is at an intermediate level; and
if the measured BrAC is at an intermediate level, requesting an active third breath sample and measuring BrAC.

9. The method of claim 8, wherein actively obtaining a second air sample from the driver further comprises:
requesting, through a human-machine interface, an undiluted breath sample directed towards the BrAC sensor.

10. The method of claim 9, further comprising:
sending a result of the driver's BrAC measurement to a central processing unit (CPU), wherein the CPU is in communication with the vehicle.

11. The method of claim 1, further comprising:
disabling the operation of the vehicle if the result of the driver's BrAC measurement is above a high set point.

12. The method of claim 1, further comprising:
enabling the operation of the vehicle if the result of the driver's BrAC is below a low set point.

13. The method of claim 8, further comprising:
requesting and actively obtaining a second air sample from the driver and measuring the BrAC of the driver if a BrAC result from the first air sample is at the intermediate level.

14. The method of claim 1, further comprising:
continuously measuring air samples after initiating the sensor system; and
continuously measuring the concentration of the tracer gas after the first air sample is measured.

15. An apparatus for passive breath alcohol detection for vehicle operation, the apparatus comprising:
sensors configured to measure a concentration of a tracer gas in a passively obtained first air sample of air in a vehicle; and
a processor configured to:
monitor at least one testing condition affecting the ambient air inside the vehicle;
determine if the at least one testing condition is within a predefined range;
if the at least one testing condition is within the predefined range and a peak in tracer gas concentration is detected, measure a Breath Alcohol Concentration (BrAC) from the first air sample;
if the at least one testing condition is outside of the predefined range, request and actively obtain a second air sample from a driver of the vehicle and measure the BrAC of the driver.

16. The apparatus of claim 15, further comprising:
a timer configured to:
measure a time interval between initiating the sensors and detecting the peak in tracer gas concentration, and wherein the processor determines that the at least one testing condition is outside of the predefined range if the time interval exceeds a predetermined time limit.

17. The apparatus of claim 15, wherein the sensors are further configured to:
measure the environmental conditions of a vehicle.

18. The apparatus of claim 17, further comprising:
a temperature sensor configured to:
measure a temperature within the vehicle, and wherein the processor determines that the at least one testing condition is outside of the predefined range if the temperature is outside a predetermined temperature range.

19. The apparatus of claim 17, further comprising:
a pressure sensor configured to:
measure a pressure within the vehicle, and wherein the processor determines that the at least one testing condition is outside of the predefined range if the pressure within the vehicle is outside a predetermined pressure range.

20. The apparatus of claim 15, further comprising:
a camera configured to measure the driver's head position relative to a BrAC sensor.

* * * * *